United States Patent
Alshammari

(10) Patent No.: US 11,317,906 B2
(45) Date of Patent: May 3, 2022

(54) SUTURE GUIDE AND TENSIONING DEVICE

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Abeer Ayed Alshammari, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 4 days.

(21) Appl. No.: 16/927,432

(22) Filed: Jul. 13, 2020

(65) Prior Publication Data

US 2022/0008065 A1 Jan. 13, 2022

(51) Int. Cl.
| | |
|---|---|
| *A61B 17/04* | (2006.01) |
| *A61B 42/20* | (2016.01) |
| *A61B 17/00* | (2006.01) |
| *A61L 31/02* | (2006.01) |

(52) U.S. Cl.
CPC ...... *A61B 17/0483* (2013.01); *A61B 17/0493* (2013.01); *A61B 42/20* (2016.02); *A61L 31/022* (2013.01); *A61B 2017/00438* (2013.01)

(58) Field of Classification Search
CPC .......... A61B 2017/00438; A61B 42/20; A61B 17/04; A61B 17/0469; A61B 17/0482; D04B 3/04; D04B 3/00
See application file for complete search history.

(56) References Cited

U.S. PATENT DOCUMENTS

| | | | |
|---|---|---|---|
| 1,246,162 A | 10/1917 | Gruman | |
| 1,282,953 A | 10/1918 | Sauer | |
| 2,244,903 A | 6/1941 | Walk et al. | |
| 2,316,031 A * | 4/1943 | Vogt | D04B 3/00 242/149 |
| 2,432,579 A | 12/1947 | Lloyd | |
| 3,246,338 A | 4/1966 | Miller | |
| 9,517,071 B2 * | 12/2016 | Fujisaki | A61B 17/12009 |
| 2007/0270885 A1 * | 11/2007 | Weinert | A61B 17/0469 606/139 |
| 2011/0092987 A1 * | 4/2011 | Gaynor | A61B 17/0482 606/139 |
| 2011/0196389 A1 * | 8/2011 | Schneider | A61B 17/0401 606/148 |
| 2014/0148824 A1 * | 5/2014 | Fujisaki | A61B 17/12009 606/144 |
| 2016/0270459 A1 | 9/2016 | Mueller, III | |
| 2019/0298335 A1 * | 10/2019 | Demir | A61B 17/0401 |
| 2021/0071328 A1 * | 3/2021 | Rees | D04B 3/04 |

\* cited by examiner

*Primary Examiner* — Katherine H Schwiker
*Assistant Examiner* — Raihan R Khandker
(74) *Attorney, Agent, or Firm* — Oblon, McClelland, Maier & Neustadt, L.L.P.

(57) ABSTRACT

A finger protector to prevent lacerations to the fingers of a surgeon during suturing. A kit comprising the finger protector and a method of using it during surgery.

20 Claims, 7 Drawing Sheets

SUTURE GUIDE AND TENSIONING DEVICE

BACKGROUND OF THE INVENTION

Field of the Invention

The invention pertains to the field of surgery, especially to a device for preventing lacerations and exposure of a surgeon to infectious agents during suturing.

Description of Related Art

The term "suture" is used to refer both to a specific technique for closing a wound in which the sides of the wound are stitched together and to the individual stitches involved in the wound closure. Sutures describe the actual thread, filament, closure or material that closes a wound, whereas stitching usually refers to a medical procedure of closing a wound.

Many surgical procedures require the use of sutures to join lacerated or wounded tissues and often require a surgeon to carefully manipulate the sutures using fingers or finger joints as shown in FIG. 1 (Zollinger's Atlas of Surgical Operations). However, when a suture is placed under tension in order to secure a stitch and tie, and cut off residual suture as shown in FIG. 2 (Zollinger's Atlas of Surgical Operations), it can cut or damage a surgeon's hand as shown by FIG. 3. Common types of such threading/suturing injuries include the lateral part of distal and middle phalanx joint of the index finger which is often used to apply tension while threading/suturing.

Such damage exposes the surgeon to infectious agents such as hepatitis viruses, HIV that can be transmitted by exposure to patient blood or other bodily fluids, including chest fluids, can cause other infections such as COVID 19. It can also expose a patient to an infectious agent carried by a surgeon.

Surgical stitching is distinguishable from conventional sewing and knitting in many ways. Surgical stitching involves joining tissues, not fabrics, together. Skin is thicker than many fabrics and is moist unlike fabric condition during most sewing or knitting. Moreover, unlike sewing needles, surgical needles are maneuvered using sterile surgical instruments such as forceps or needle holders, not by hand.

Surgical needles come in a variety of sizes and shapes including nearly invisible microsurgical needles, blunt needles for stitching delicate, easily damaged tissues, and specialized needles that are super-sharp and spatula-shaped for eye surgery.

Surgical sutures, surgical threads, and surgical wires also have a variety of different structures and textures not found in sewing or knitting materials.

In conventional sewing a number of devices have been devised to feed, hold or manipulate sewing thread or yarn. These include thimbles, hand or finger coverings and devices to feed or separate different threads or yarns. Manual knitting accessories for guiding yard are described by U.S. Pat. No. 2,244,903 and a device for putting yarn under tension is disclosed by U.S. Pat. No. 1,243,162. A protective device for use in hair-threading is disclosed by U.S. Patent Pub. 2016/0270459. However, these devices are not designed for, or suitable for surgical usage. They are bulky, often made of materials that are difficult to clean or sterilize, and are not structurally configured to manipulate or tension surgical sutures during complex surgical procedures requiring a high degree of training and dexterity.

In contrast to conventional sewing, surgical suturing, such as suturing closure of an abdominal wall involves multiple layers of skin tissues including subcutaneous tissue, muscle tissue and fascia. Each type of tissue requires a different degree of tension during suturing and a surgeon relies on tactile sensitives through the fingers and hands to properly control the amount of tension. For example, the fascia of the abdomen in a laparotomy or the chest wall muscle in a thoracotomy is tough and difficult to suture. Typically two surgeons are required to properly suture it, one to handle the needle and process the suturing and the other (usually an assistant) to maintain the suture under tension. This type of procedure requires a thick type of suture such as no absorbable Prolene or polydioxanone suture (PDS) which is sharp and can cause lacerations to the surgeon who keeps it under a required degree of tension. The need to maintain tension is attributable to intra-abdominal pressure which can lead to wound dehiscence and risk of hernia if suturing is not properly handled. Compared to conventional fabric sewing, which is done by hand or by sewing machine, suturing requires careful control of intra-abdominal pressure created by abdominal organs and heart, see FIG. 3C. In conventional sewing it is unnecessary to keep the threads or fabric under tension because there is no equivalent of intra-abdominal pressure to manage. Moreover, imposing tension during conventional sewing can damage the stitching or fabric.

In view of the problems which are associated with surgical procedures requiring placing suturing under tension, including damage to surgical gloves and to a surgeon's hands and the need to maintain a high degree of dexterity for the surgeon while suturing tissues, the inventors designed and developed a device that protects a surgeon's finger from lacerations and surgical site infections and which provides for close control of sutures under tension during surgical procedures.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One aspect of the invention is directed to a surgical device that protects a surgeon's fingers and finger joints from abrasions and lacerations caused by handling of sutures during a surgical procedure as well as to surgical kits containing the device.

The device comprises an open ring (e.g., adjustable ring) which is worn over one or more fingers by a surgeon during an operation (e.g., a surgical procedure involving stitching of tissue), a plate (protective plate) attached to the outside circumference of the open and/or adjustable ring, and a hook (e.g., an angulated tip or grasping protrusion) designed to permit the surgeon to manipulate sutures, threads and wires during surgery without direct contact between the suture and the surface of a finger or finger joint. The open ring may be configured to permit easy mounting on a finger or segment of a finger and adjustment to an appropriate finger size. The open ring may be worn on the left or right hand and, depending on the preference or handedness of the wearer, may be worn so that a suture may be threaded into the hook (e.g., configured as an open eye) from either the left or right. The width of the open/adjustable ring preferably ranges from about 2, 3, 4, 5, 6, 7, 8, 9 to 10 mm and with a preferable thickness of from about 1, 2, 3, to 4 mm. The open ring may have a gap ranging from about >0 to about 2.5 cm. Preferably the ring is in contact with and covers the sides of the finger and portions of the ventral surface of the finger. However, it a portion of the ventral surface may be left. Typically, a suture or surgical thread is held under tension on the dorsal aspect of the finger and can sometimes overlap and cover both ventral and dorsal surfaces.

In some embodiments the ends of the open ring may be in contact (but not joined) with one another (no gap) and in other embodiments the ends may overlap (no gap), for example, by up to >0, 0.2, 0.5, 1 or 1.5 cm. This overlap can provide greater play or ability to expand the size of the ring to fit a larger finger. The thickness of the ring or its composition may be selected to provide sufficient flexibility for the ring to expand when mounted on a finger prior to use. Preferably, the ring is snugly fit to the finger to provide a firm base for its use in suturing.

In a preferred embodiment, the device has a diamond-shaped or parallelogram-shaped protective plate, which may have slightly curved edges or vertices, to protect finger areas used to apply tension during stitching and suturing. The diamond-shape covers areas at risk of injury but does not cover areas of the finger needed for receiving tactile sensations from a tissue.

In some embodiments, the edges or vertices of the plate may be curved by up to 1, 2, 5, 10, 15, 20, 25 or <25 degrees toward the surface of the open ring. For example, for the two corners of a diamond-shaped plate that are in the plane defined by the ring may be curved downward toward the ring as shown by FIG. 4E.

Advantageously, the hook is configured to hold a suture, thread or wire under tension without the risk of lacerating the finger. The hook has an eye on one side of the shank which connects it to the plate. The eye has a gap on its lower side which permits a suture to be treaded upwardly into the eye. One example of the hook is shown in the figures which depict a P-shaped hook with an L-shaped channel comprising a gap in the lower part of the P's loop and a gap between the lower side and the plate. In alternative embodiments, a hook may have a different shape but comprise a shank, stem or leg attaching it to the plate and comprising an L-shaped channel which permits insertion of a suture from a lower proximal (to the finger) position into an eye which secures the suture laterally against either side of the eye and distally (to the finger) against the top side of the eye when tension is applied. In some embodiments the hook is fixed on the side on which the thread or suture will be hung. In other embodiments the hook can rotate clockwise or counterclockwise and then be fixed or locked at a specific position depending on the needs, handedness, and preference of the user.

The open eye permits suture material to be upwardly threaded into it, and then placed under tension by moving the device laterally or proximally toward the surgeon. Tension on a suture may be released by moving the finger holding the device distally. The open eye, which is closed on its top and open on its bottom, prevents upward disengagement of a suture material when tension is applied to a suture.

The hook feature permits a continuous threading, holding and easy release of the suture and repeat of this cycle until an entire wound is sutured. Preferably, the hook is mounted in the middle of the plate which maintains balance of the device and permits the surgeon to use the thumb to move the protector to the other side when not in use.

Another aspect of the invention is directed to a safer and improved surgical method, or surgical training method, using the device disclosed herein to handle surgical sutures, threads and wires. Surgical methods using this device are safer because the avoid the risk of damage to surgical gloves and skin surfaces by thin surgical sutures, threads or wires, especially during procedures requiring the application of tension to the distal ends of these materials such as in many abdominal surgeries. This makes an operation safer for both the surgeon and the patient as it avoids contact and cross-contamination of bodily fluids that can carry viruses like HBV, HCV and HIV or other pathogens.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings below.

Figure 1:
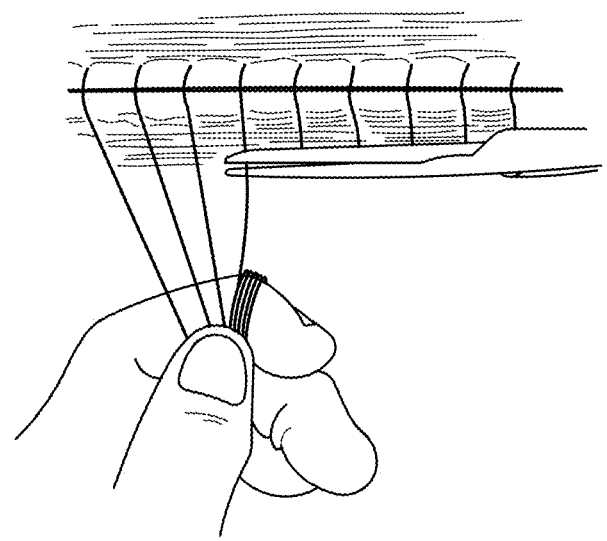
FIG. 1 depicts several ends of sutures wrapped around the distal finger joint.

The dimensions of the shank 405 and the other members forming the eye and gaps 425 and 428 can be selected based on a type and dimensions of a suture to be used and the personal preferences of a surgeon. In some embodiments, the shank of the hook 405 ranges from about 0.3 to 0.8 mm in height, about 0.1 to 0.8 mm in width (thickness), preferably about 0.5 to 0.76 mm for strength and durability, the top side of the hook 410 ranges in length from 0.3 to 0.7 mm and ranges in height (thickness) from 0.1 to 0.8 mm, preferably about 0.5 to 0.7 mm for strength and durability, the lateral side of the hook 415 ranges in height from about 0.4 to 0.6 mm and ranges in width (thickness) from about 0.1 to 0.8 mm, preferably about 0.5 to 0.7 mm for strength and durability, and the bottom side 420 ranges in width from about 0.2 to 0.5 mm and in height (thickness) from about 0.1 to 0.4 mm. The opening 428 in the bottom side 420 can range in width about 0.1 to 0.3 mm and the distance 425 between bottom side 420 and plate 300 can range from about 0.1 to about 0.3 mm.

Figure 4A:
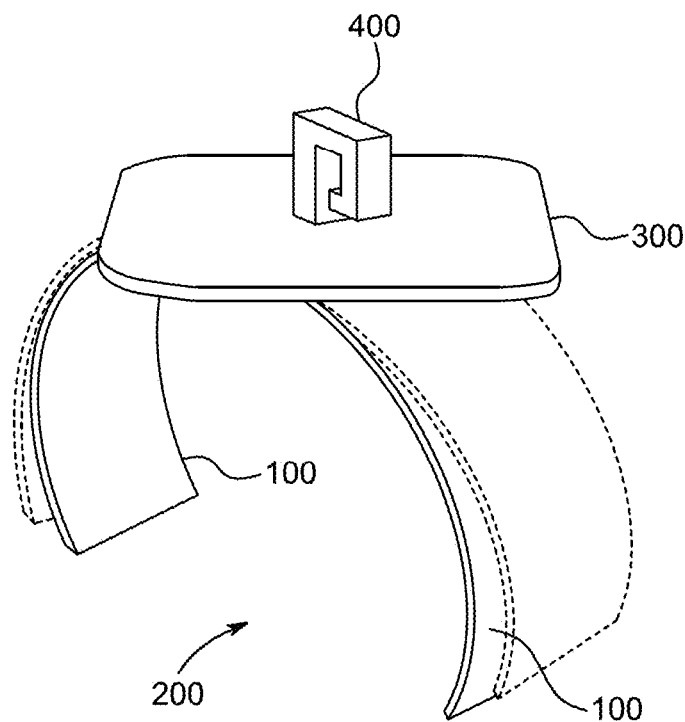
FIG. 4A illustrates some basic elements of the device disclosed herein including an open ring (finger holder) 100, adjustable gap 200 between the two ends of the open ring, a plate (protective plate) 300 and a hook (angulated tip, suture holder) 400. As shown, the ends of ring 100 are flexible and can adjust to different finger sizes.
Figure 4B:
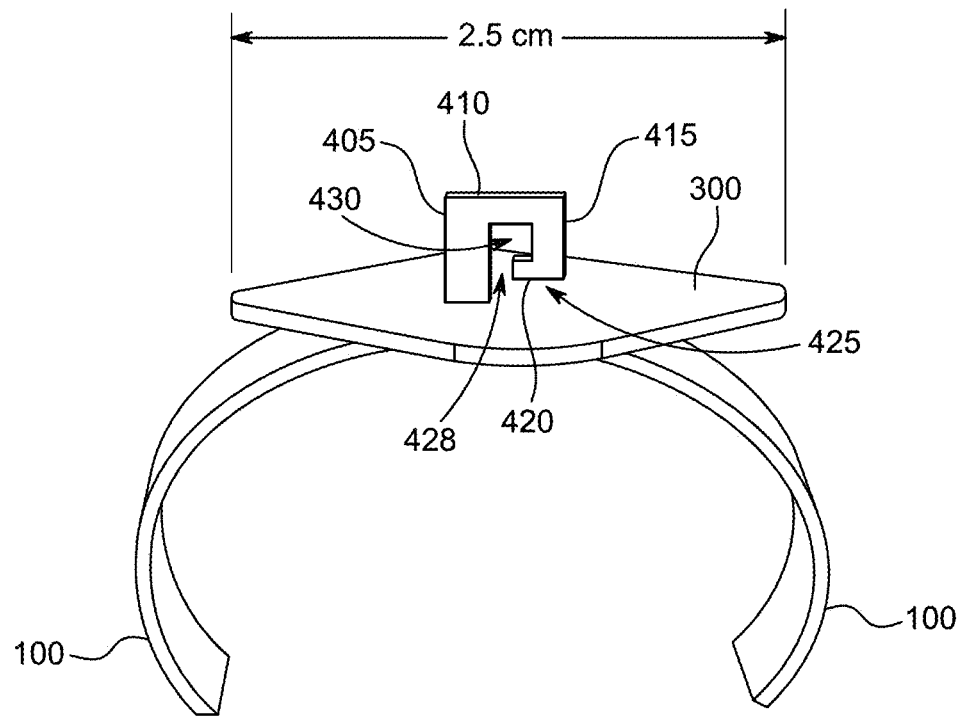
FIG. 4B provides detail of the hook (angulated tip, suture holder) element 400. As shown the plane of the hook is aligned with the 2.5 cm diagonal of a diamond-shaped plate 300. The eye of the hook is aligned with the other diagonal of the plate. The shank (foot, stem, leg) of the hook 405 connects it to the plate and is attached to a top 410, lateral 415 and bottom 420 side of the hook defining open eye 430. The opening 428 in the bottom side 420 together with a gap between the lower side 420 and plate 300 forms an L-shaped channel through which suture material may be threaded into and held in eye 430.
Figure 4C:
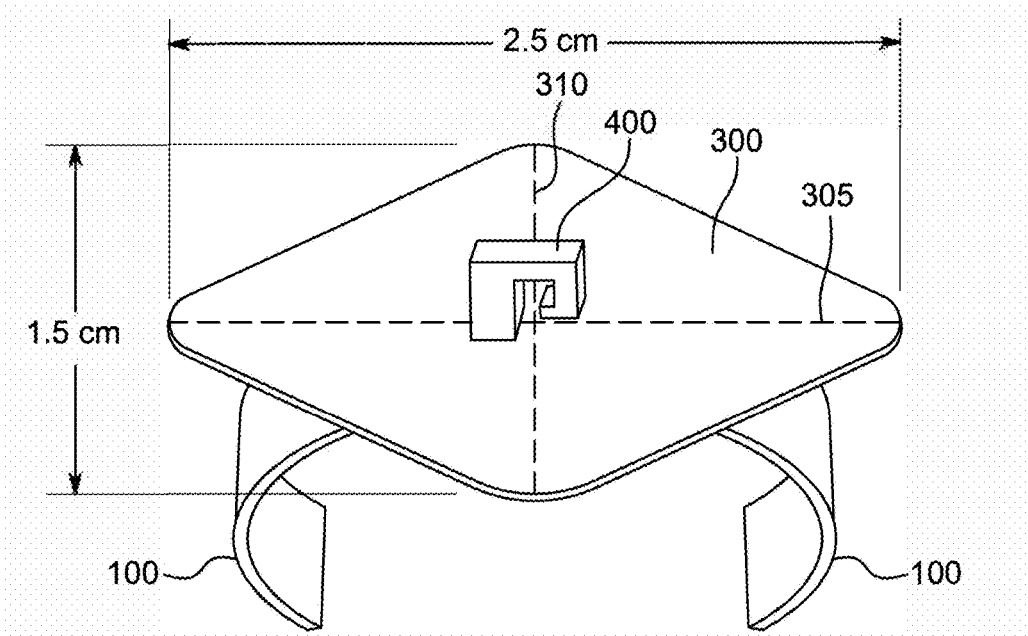

FIG. 4C illustrates a device having a diamond-shaped plate comprising open ring 100, plate 300, which has a minor diagonal that is 1.5 cm long and a major diagonal that is 2.5 cm long each indicated by dashed lines. 305 and 310, respectively. The plane of the hook is aligned with diagonal 305 and the eye with diagonal 310.

Figure 4D:
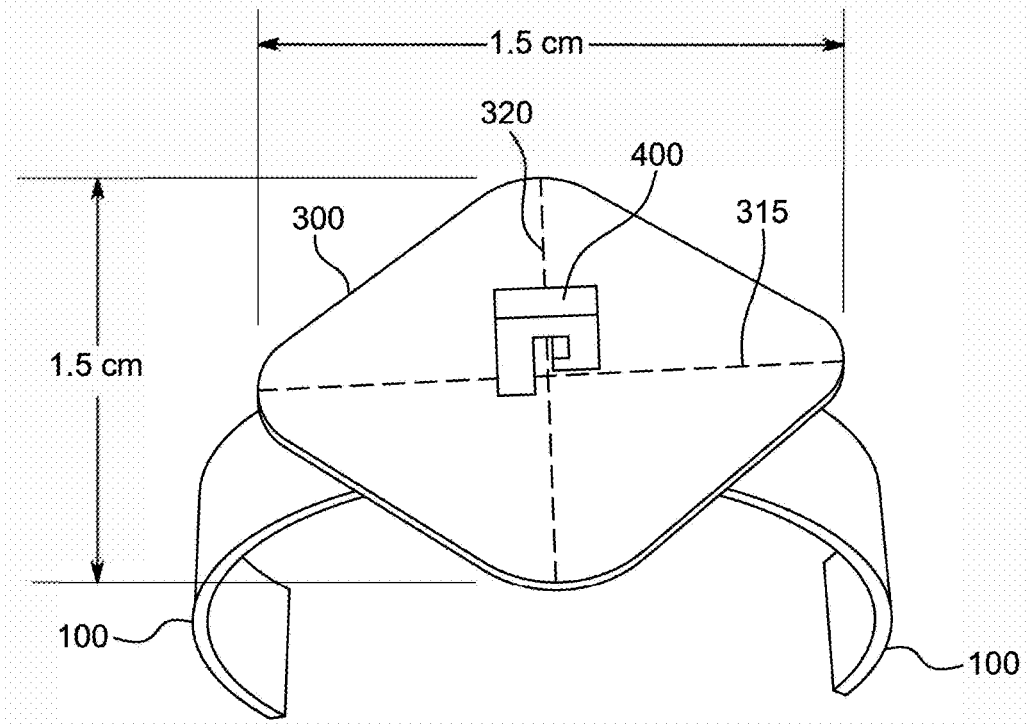

FIG. 4D illustrates a device having a square plate with rounded vertices having diagonals 315 and 320 that are each 1.5 cm long and which comprises open ring 100, plate 300, and hook 400.

Figure 4E:
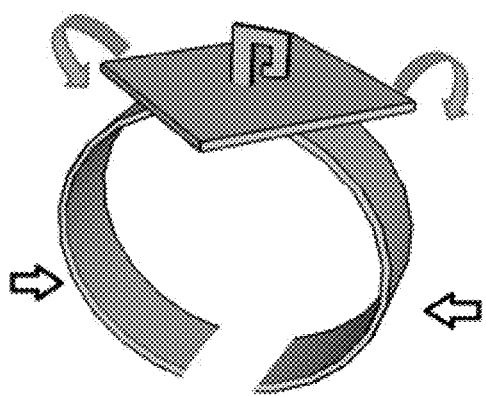
Figure 5A:
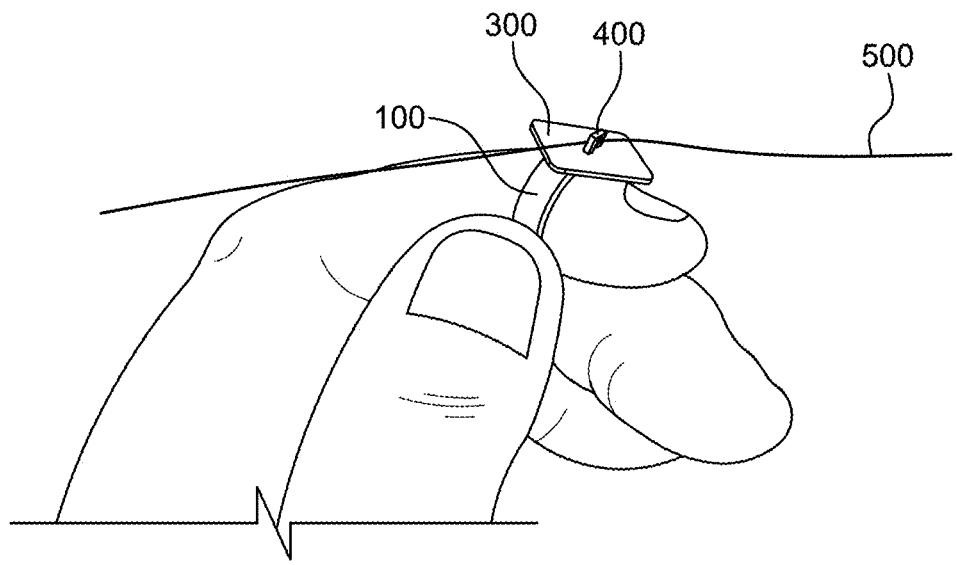

FIG. 4E depicts vertices of the plate which can be rounded or curved (upper arrows) and the flexible ends of ring 100 which can be compressed inward (lower arrows) to fit a smaller finger FIG. 5A shows a suture 500 threaded over the plate 300 and through hook 400. Open ring 100 is sized or adjusted to fit snugly over the distal finger joint.

Figure 5B:
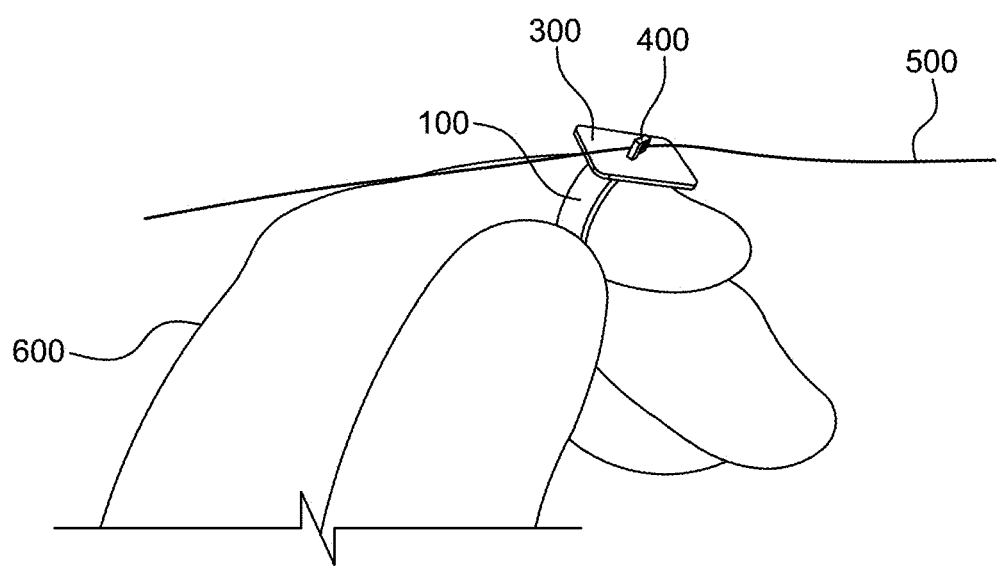

FIG. 5B shows a suture 500 threaded over the plate 300 and through hook 400. Finger holder 100 is sized or adjusted to fit snugly over the glove 600 covering the distal finger joint.

DETAILED DESCRIPTION OF THE INVENTION

Figure 2:
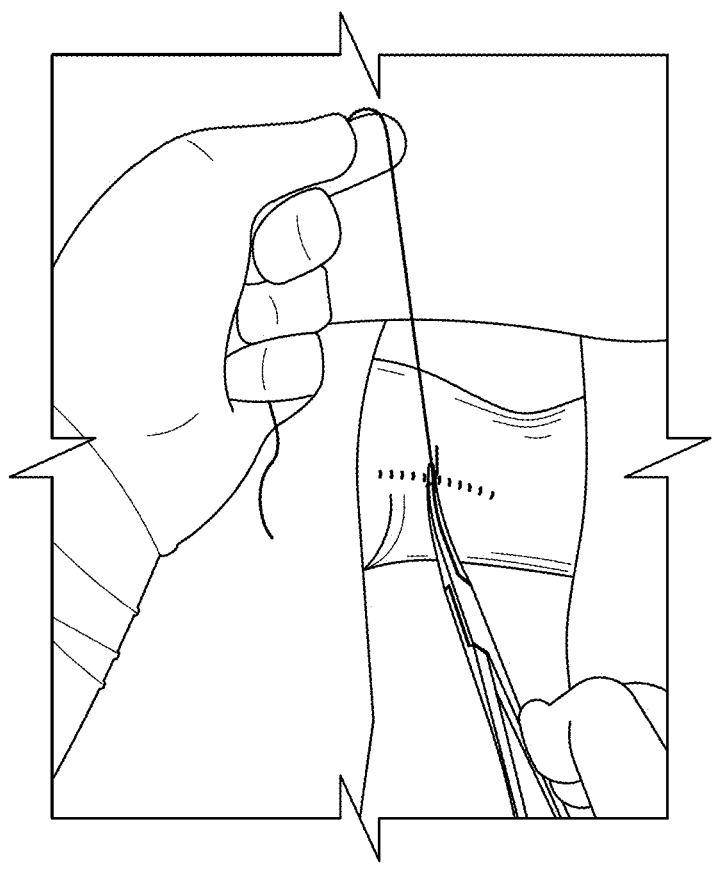
FIG. 2 shows suture material held under tension over an index fingertip.
Figure 3A:
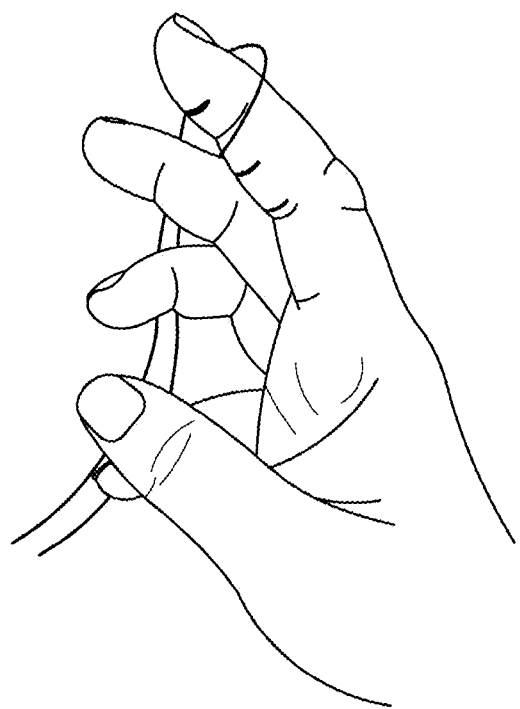
FIG. 3A shows a hand lacerated by suturing.

Injuries to surgeons during surgery are a continuing problem for surgeons, especially in surgical procedures where a suturing material must be kept under tension, for example, to prevent wound dehiscence or herniation in abdominal surgery. Some types of suturing materials are more likely to inflict finger wounds under these circumstances including prolene a type of synthetic, monofilament, nonabsorbable polypropylene suture often used for skin closure and general soft tissue approximation and ligation. Sometimes small lacerations or finger wounds are not noticed until after surgery thus making it difficult to take effective prophylactic action and thus presents a high risk to a debilitated or immunosuppressed patient. Other procedures requiring suturing, such as veterinary surgery, also experience this problem. FIGS. 1 and 2 describe some surgical procedures in which a surgeon (or patient) is at risk and FIG. 3 depicts some locations which frequently are damaged by wounds (thread injuries) caused by suturing materials.

While surgical gloves provide some protection against lacerations caused during suturing, bulky surgical gloves cause difficulty in handling surgical instruments and reduce surgical dexterity and sensitivity. Surgical performance is further impaired when a surgeon double gloves the hands for a patient who is infected with HBV, HCV, HIV, COVID-19 (SARS-CoV-2), or another infectious agent. Generally, the device may be worn over any regular or conventional sterile surgical gloves, such as latex or vinyl gloves, which have a thickness that preserves tactile sensitivity during surgery.

Disclosed is a compact surgical device useful for placing or keeping a suture material (suture, thread, surgical wire) under tension, adaptable to different finger sizes or positions, can be worn over a glove, can be easily sterilized for use in multiple procedures, and which provides protection against cross-infection between doctor and patient.

The device is economic because it is inexpensive to make and its use reduces the risk and costs of cross-infections, including financial costs of treating a cross-infected patient or surgeon or the costs of isolation, quarantine or suspension from duties of an infected person.

Figure 3B:
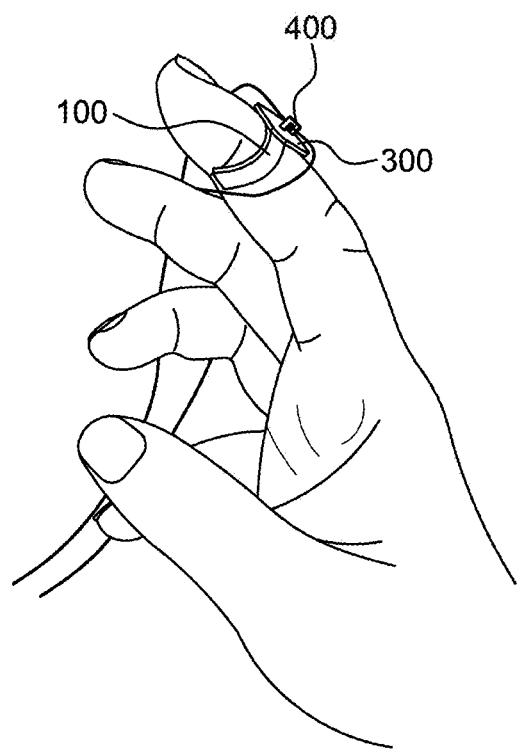
FIG. 3B depicts a hand similar to that in FIG. 3A that is protected by a device as disclosed herein.
Figure 3C:
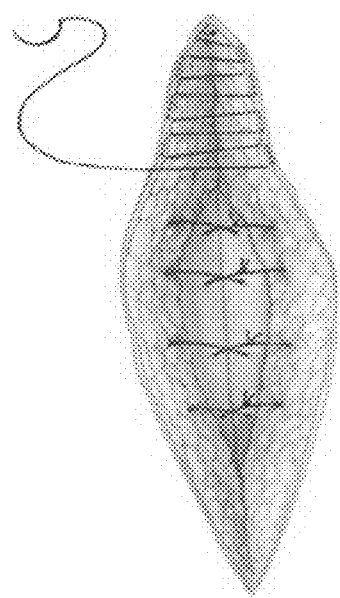
FIG. 3C depicts a surgical wound that is partially sutured illustrating the requirement for placement of sutures under tension.

FIG. 3B shows one embodiment of the device as worn over a gloved distal interphalangeal (DIP) finger joint. The open ring 100 of the device is adjustable permitting the device to be worn over segments of the finger susceptible to thread injury; see FIG. 4A which describes the gap 200 in the open ring of the device. The size of the gap can be increased or decreased depending on the finger size of the wearer or on the segment of the finger being protected based on the flexibility of the open ring 100. For many procedures, the device is worn over the index finger. The flexible ring may be flexible on both ends or on one end only. The device is used in procedures requiring handling of sutures, surgical thread, or surgical wires.

Typically, as also shown by FIG. 4B, the open eye 430 of the hook 400, is aligned with the longitudinal axis of the open ring 100 which fits over a finger. The open eye points in the same direction as the finger. The elements of the device, the adjustable open ring 100, plate 300 and hook 400 may be assembled and welded or glued together or in an alternative embodiment, may be cast or 3D printed as a single piece. Preferably, the device is assembled from two metal pieces: the plate with the attached hook (angulated tip) and the open ring.

In some embodiments, the plate 300 or the hook 400 may be adjustable and can be loosened, placed at a different rotational angle between 0, 45, 90, 135, 180, 225, 270, 315, and 360 degrees, and retightened. This feature permits a surgeon to select a configuration suitable for a particular procedure or based on her own preferences. In many embodiments, the suture when placed into the eye is secured under tension by grasping it. In some embodiments, the device may be twisted or rotated to hold the suture in the eye or lock it though this may lengthen the time required for suturing. In some embodiments at the end of a surgery, such as a minor surgery, a lone surgeon can wear the device on an index finger and manipulate the needle using the ring finger and thumb.

FIG. 4C shows an embodiment where a major (longer) diagonal 305 of the plate is 2.5 cm. The plane of the hook is aligned with the major diagonal and the eye of the hook is perpendicular to it. The hook (400) is preferably about 0.5 cm wide and high.

FIG. 4C shows an embodiment where a major (longer) diagonal of the plate is 2.5 cm and is aligned perpendicular to the open square eye of the hook and where the minor (shorter) diagonal of the plate is aligned with the open square eye of the hook.

FIG. 4D shows an embodiment where a diagonal of the plate is 1.5 cm and is aligned with the open square eye of the hook.

FIG. 5A shows a suture 500 threaded over the plate 300 and through hook 400. Open ring (finger holder) 100 is sized or adjusted to fit snugly over the distal finger joint and FIG. 5B shows the device as worn over a gloved hand.

Aspects of this technology include, but are not limited to, the following.

One aspect of this technology is directed to a finger protector suitable for use in surgery or surgical training which comprises an open ring having a gap, a plate anchored or attached to an outside surface of the open ring, and a hook (grasping protuberance) with its shank perpendicularly attached to the outside surface of the plate, wherein the hook is configured to hold and release a suture, thread, or wire. The open ring has a gap the size of which can be increased or decreased to fit a particular finger or segment of a finger or to allow it to be worn by surgeons having different finger sizes. Typically, the open ring comprises or is made of a flexible material, such as a flexible metal or thermoplastic polymer, which permits the gap to be adjusted by moving one or both ends of the ring to enlarge or reduce the gap. The open ring can be made of a flexible metal, a malleable metal or a metal that can undergo strain and revert to its original shape (or snugly fit a finger) when the strain is removed.

Similarly a ring comprising plastic, resin, or thermoplastic can be produced from a material that can undergo strain but revert to its original shape once strain is removed. In other embodiments, the ring may comprise stainless steel or another durable, flexible metal alloy.

Preferably, the ring as well as the other elements of the device are made of materials that can be heat or steam sterilized, for example, in an oven or autoclave, sterilized with radiation, or which are stable under conditions of low temperature sterilization such as with ethylene oxide gas hydrogen peroxide gas plasma, peracetic acid immersion, or ozone).

One or more elements of the device disclosed herein may comprise metals or metal alloys containing copper, nickel, iron, titanium, aluminum, platinum, silver, or gold. Other durable alternative metals used to make jewelry rings such as cobalt, stainless steel, sterling silver, tungsten, ceramic carbide may be used to make one or more elements of the device disclosed herein.

In another embodiment, the open ring, or in some alternative embodiments a closed ring, may be custom made for a particular person's finger or in a variety of standard ring sizes. It may have beveled edges for easy adjustment and overlap for a surgeon with small fingers. Typically, the ring is a durable metal or alloy that will not be broken by simple tension or traction. The use of devices which are breakable during surgical procedures is dangerous as their fragments may be left inside of a patient and due to loss of functionality once broken. Preferably the ring comprises titanium, copper or gold. In some alternative embodiments, the ring may comprise other durable materials that can be sterilized. These include rings made from durable, heat-resistant plastics and hook-in-loop fasteners such as Velcro® brand fasteners. In some embodiments, especially when non-metallic materials are used to make the ring, the ring may be configured to attached to the plate and be disposable after each use.

The open ring of the device disclosed herein may be designed or configured to fit over a distal interphalangeal (DIP) joint or a proximal interphalangeal (PIP) joint on an index finger or other finger or thumb. In some embodiments, the diameter of the open ring when off or on a finger ranges from 10, 15, 20 to 25 mm and the thickness of the open ring ranges from 1, 2, 3, 4, or 5 mm or any intermediate value within these ranges.

The plate component of the device disclosed herein typically comprises a hard metal such as stainless steel or a metal or metal alloy that has a scratch hardness of at least 3, 4, 5 or 6 as measured on the Mohs scale. Preferably the components of the device are metallic as this permits sterilization by autoclave and reuse. Also, the device may be made radiopaque (e.g., by use of steel or titanium) which facilitates location of the device should it be lost inside a patient.

In some embodiments, the plate is smooth or has a coating, such as polytetrafluoroethylene (PTFE) which reduces its coefficient of friction in comparison to an uncoated plate. Similarly, the open ring component or the hook component may comprise such a coating. In a preferred embodiment, the plate has a thickness ranging from 1, 2, 3, 4, or 5 mm. The plate may have tapered or rounded edges or vertices for safety. In preferred embodiments, the protective plate has two lateral edges which are founded to cover the lateral sides of the finger. In other embodiments, a thin rubber layer with an adhesive part, is fixed over the plate and can be removed before cleaning and sterilization. This protects the device from damage between uses. When left on during use, this layer increases the friction of the surface to more easily hold a surgical thread or suture in place and prevent it from slipping off the plate. In other embodiments, the plate and ring do not have a coating.

The plate element of the surgical finger protector is substantially flat or planar and may have any suitable shape, but preferably is diamond-shaped or parallelogram-shaped with one diagonal aligned with the finger and the other aligned with the plane of the ring as shown in FIGS. 4A-4D and 5A and 5B.

The shape of the plate is selected to cover the area of suture tension that would otherwise be on the surface of the finger. In one embodiment, the surgical finger protector comprises a flat plate having a shape of a parallelogram having a minor and major diagonal, wherein the minor diagonal ranges in length from 1.0, 1.25, 1.5, 1.75 to 2.0 cm and wherein the major diagonal ranges in length from 2.0, 2.25, 2.5, 2.75 to 3.0 cm or any intermediate value with these ranges. Preferably, the parallelogram has diagonals of 1.25× 2.5 cm.

In another embodiment, the shape of the plate is square with the length of its diagonals between 1.0, 1.5, 2.0, 2.5 to 3.0 cm.

The hook element attached to the outer (upper) surface of the plate, which is most distal surface to the finger when the device is worn. The hook comprises a shank the end of which is anchored and/or attached to the plate and/or through the plate to the ring, and also comprises structural elements defining an open eye, which are attached to the upper part of the shank.

The structural elements defining the eye may be arranged at right angles to each other and to the shank as shown in FIGS. 4A-4D and form a substantially rectangular or square eye having an opening on a side horizontal to the surface of the plate. This eye opening permits a suture, thread or wire to be threaded into the eye from below. The eye has only the lower opening, so it is impossible for the suture material, thread or wire to escape upwardly. Once threaded into the eye, the suture material can be put under tension by pulling the finger away from the suture. The suture material cannot be released from the top of the eye, but can be released by relaxing the tension so as to permit the suture material to exit the eye via its lower opening.

Another aspect of this technology is directed to a method for handling a surgical suture, thread or wire comprising wearing the device on a finger and threading the suture, thread or wire into the hook of the device disclosed herein, and suturing one or more tissues. In one embodiment, this method comprises performing a laparotomy.

Surgical procedures. The device of the invention may be used in conjunction with a variety of different surgical procedures requiring suturing. Surgical procedures include wound closure, such as closure of wounds in skin or other tissues. Suturing techniques include those described by David L. Dunn, ed. (2007). *Wound Closure Manual*. Johnson & Johnson (hypertext transfer protocol://web.mit.edu/2.75/resources/random/ethicon_wound_closure_manual.pdf, last accessed Jun. 4, 2020). In a preferred embodiment, the device is used in abdominal surgery or for laparotomy.

A laparotomy typically involves a surgeon handling a forceps, which is used to grab the tissue to be sutured, and a needle which is used to suture the tissue. An assistant surgeon can hold the suture or surgical thread and keep it under tension which is essential to prevent herniation of wound dehiscence. When each stitch is taken, the assistant surgeon releases tension on the thread for a few seconds and then holds it in the same degree of tension again while the surgeon applies another stitch. This cycle is repeated until the entire wound is sutured. The device as disclosed herein is used by the assistant surgeon to apply tension and release it during this surgical procedure.

Sutures. The device of the invention may be used for handling of a variety of different types of sutures, surgical threads or surgical wires. A medical professional will select an appropriate suture material based on the nature and demands of a surgical procedure, including the location and size of a wound. Suture materials include, but are not limited to, absorbable and non-absorbable materials, monofilament or braided materials, and natural or man-made materials.

Gut is a natural, monofilament suture material often used to repair internal soft tissue wounds or lacerations, such as those occurring in gynecological surgery; however it is not used for cardiovascular or neurological procedures and avoided for cosmetic surgery due to the risk of a body reacting to this material and scarring over.

Polydioxanone or PDS is a synthetic, monofilament suture material and used for repair of many types of soft tissue wounds, including abdominal closures and for pediatric cardiac closures. PDS sutures are ideal for use in general orthopedic surgery, sub cuticular, gastro intestinal tract, pediatric cardiovascular surgery, sheath closure and general surgery and cause minimal tissue reaction. Polydioxanone suture provides wound support for longer period as compared to other synthetic absorbable sutures and offers superior tensile strength and pliability. Polydioxanone sutures retain about 70% of the initial tensile strength after 2 weeks, 50% of the initial tensile strength after 4 weeks and 25% after 6 weeks of implantation and the suture is essentially absorbed within 180 days.

Poliglecaprome (MONOCRYL®) is a synthetic monofilament, absorbable suture material generally used for soft tissue repair and can be used to invisibly close tissues, however its use is avoided in cardiovascular or neurological procedures. It is available dyed violet or undyed (clear). Monocryl has a low tissue reactivity, maintains high tensile strength, and has a half-life of 7 to 14 days. At 1 week, its in vivo tensile strength is at 50-60% undyed (60-70% dyed), 20-30% undyed (30-40% dyed) at two weeks, and essentially completely hydrolyzed by 91-119 days.

Polyglycolic-acid sutures may be single filament or braided. VICRYL® (polyglactin 910; PubChem CID 71391) is an absorbable, synthetic, usually braided suture, manufactured by Ethicon. A monofilament version is also made for use in ophthalmic practice. It is indicated for soft tissue approximation and ligation. The suture holds its tensile strength for approximately two to three weeks in tissue and is completely absorbed by hydrolysis within 56 to 70 days. Polyglactin is a coated, braided, multifilament suture like polyglycolic acid. VICRYL® suture has similar handling properties to polyglycolic acid but has more tensile strength. Other brands of polyglycolic acid sutures include POLYSYN®, SURGICRYL®, POLYSORB®, AND DEXON®.

Other suture materials, their structures and properties, and criteria for their selection for particular surgical procedures are described by and incorporated by reference to David L. Dunn, ed. (2007). *Wound Closure Manual*. Johnson & Johnson (hypertext transfer protocol://web.mit.edu/2.75/resources/random/ethicon_wound_closure_manual.pdf, last accessed Jun. 4, 2020). Some preferred suture materials include prolene, PDS, and materials having lacerating surfaces or cross-sections, including those having a silk size ranging from 0, 1 to 2.

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Spatially relative terms, such as "under", "below", "lower", "over", "upper", "in front of" or "behind" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A surgical finger protector, comprising:
   an open ring having a gap,
   a plate anchored to an outside surface of the open ring, and
   a hook having a shank substantially perpendicularly attached to an outside surface of the plate,
   wherein the hook is configured to hold and release a suture, thread, or wire;
   wherein the hook is positioned in the middle of the plate; and
   wherein the position of the hook on the plate is in alignment with the open ring.

2. The surgical finger protector of claim 1, wherein the open ring comprises a flexible material and wherein the size of the gap in the ring can be adjusted.

3. The surgical finger protector of claim 1, wherein the open ring is made from a metal.

4. The surgical finger protector of claim 1, wherein the open ring is made from stainless steel.

5. The surgical finger protection of claim 1, wherein the open ring is configured to fit over a distal interphalangeal (DIP) joint or a proximal interphalangeal (PIP) joint.

6. The surgical finger protector of claim 1, wherein the diameter of the open ring ranges from 10 to 25 mm and the thickness of the open ring ranges from 1 to 5 mm.

7. The surgical finger protector of claim 1, wherein the plate is metal.

8. The surgical finger protector of claim 1, wherein the plate is a metal or metal alloy that has a scratch hardness of at least 3 as measured on the Mohs scale.

9. The surgical finger protector of claim 1, wherein the plate is smooth or comprises a coating which reduces its coefficient of friction compared to the uncoated plate.

10. The surgical finger protector of claim 1, wherein the plate has a thickness ranging from 1 mm to 5 mm.

11. The surgical finger protector of claim 1, wherein the plate has a shape of a parallelogram and wherein a diagonal of the parallelogram is tangent to the circumference of the open ring.

12. The surgical finger protector of claim 1, wherein the plate has a shape of a parallelogram having a minor and major diagonal, wherein the minor diagonal ranges in length from 1.0 to 2.0 cm and wherein the major diagonal ranges in length from 2.0 to 3.0 cm.

13. The surgical finger protector of claim 1, wherein the plate is square or square with rounded edges, and wherein a diagonal of the square ranges in length from 1.0 to 3.0 cm.

14. The surgical finger protector of claim 1, wherein the shank of the hook is attached at its proximal end to the plate and at its distal end comprises an open eye which can hold a suture, thread or wire.

15. The surgical finger protector of claim 14, wherein the open eye is rectangular and is open on a side proximal and horizontal to the plate.

16. The surgical finger protector of claim 15, wherein the outside surface of the ring is flat, wherein the plate is tangentially anchored to the outside surface of the open ring, and wherein the plate has a flat top surface such that a first axis of the plate is axially aligned with an axis of the ring, and a second axis of the plate that is perpendicular to the first axis is perpendicular to the axis of the ring.

17. The surgical finger protector of claim 15, wherein the open eye is square and is about 0.5 mm on each side.

18. A method for handling a surgical suture, thread or wire comprising inserting a finger through the open ring and threading the suture, thread or wire into the hook of the surgical finger protector of claim 1.

19. The method of claim 18, wherein said method comprises suturing a laparotomy, suturing in an abdominal surgery, or both.

20. A surgical kit, comprising a plurality of surgical finger protectors of claim 1, wherein the plurality of surgical finger protectors have open rings of different diameters which range from 10 to 25 mm.

* * * * *